United States Patent
Pelekhaty et al.

(10) Patent No.: US 7,595,874 B1
(45) Date of Patent: Sep. 29, 2009

(54) METHOD OF CONDENSED CELL SLIDE PREPARATION AND DETECTION OF RARELY OCCURRING CELLS ON MICROSCOPE SLIDES

(75) Inventors: Vladimir M. Pelekhaty, Orlando, FL (US); Anatoliy Kachurin, Orlando, FL (US); William Warren, Orlando, FL (US); Kenneth Church, Orlando, FL (US); Heather Fahlenkamp, Cleveland, OH (US); Russell Higbee, Orlando, FL (US)

(73) Assignee: Sciperio, Inc., Stillwater, OK (US)

( * ) Notice: Subject to any disclaimer, the term of this patent is extended or adjusted under 35 U.S.C. 154(b) by 180 days.

(21) Appl. No.: 11/672,794

(22) Filed: Feb. 8, 2007

Related U.S. Application Data (60) Provisional application No. 60/766,724, filed on Feb. 8, 2006, now abandoned.

(51) Int. Cl.
*G01J 3/30* (2006.01)
(52) U.S. Cl. .................................................. 356/318
(58) Field of Classification Search ................ 356/318, 356/244, 243.2, 459, 28; 436/528–535, 46; 435/288.3–288.7, 305.1–305.4; 250/458.1–461.2; 359/391–398
See application file for complete search history.

(56) References Cited

U.S. PATENT DOCUMENTS

| | | | |
|---|---|---|---|
| 2,039,219 A | 4/1936 | Hausser et al. | |
| 2,351,282 A | 6/1944 | Oliver, Jr. | |
| 3,556,633 A | 1/1971 | Mutschmann et al. | |
| 3,631,575 A | 1/1972 | Farris | |
| 4,011,350 A | 3/1977 | Markovits et al. | |
| 4,245,051 A | 1/1981 | Reich et al. | |
| 4,387,972 A | 6/1983 | Valencia | |
| 4,447,140 A | 5/1984 | Campbell et al. | |
| 4,508,450 A | 4/1985 | Ohshima et al. | |
| 4,606,244 A | 8/1986 | Schneemann | |
| 4,607,921 A | 8/1986 | Miller | |
| 4,689,307 A | 8/1987 | Schwartz | |
| 4,722,598 A | 2/1988 | Ford | |
| 4,824,247 A | 4/1989 | True et al. | |
| 4,920,017 A | 4/1990 | Herscovici | |

(Continued)

FOREIGN PATENT DOCUMENTS

JP 2000137022 5/2000

(Continued)

OTHER PUBLICATIONS

Abstract of JP2000137022 (1 page English translation).

*Primary Examiner*—Gregory J Toatley, Jr.
*Assistant Examiner*—Abdullahi Nur
(74) *Attorney, Agent, or Firm*—McKee, Voorhees & Sease, P.L.C.

(57) ABSTRACT

Detection of a rarely occurring event within one or more biological samples includes (a) processing each biological sample to provide a gellable liquid solution comprising concentrated biological sample and a flourochrome designed to associate with a rarely occurring event within the concentrated biological sample; (b) depositing the solution in a layer on a surface of a slide; and (c) scanning the solution on the slide with energy adapted to cause fluorescence of the flourochrome to detect potential instances of the rarely occurring event within the concentrated biological sample in the solution.

35 Claims, 10 Drawing Sheets

U.S. PATENT DOCUMENTS

| | | |
|---|---|---|
| 5,002,736 A | 3/1991 | Babbitt et al. |
| 5,143,714 A | 9/1992 | Cosgrove et al. |
| 5,386,318 A | 1/1995 | Kühnert et al. |
| 5,751,839 A * | 5/1998 | Drocourt et al. ............ 382/133 |
| 5,759,375 A | 6/1998 | Stein et al. |
| 5,800,691 A | 9/1998 | Kozulic |
| 5,926,266 A | 7/1999 | Dorundo et al. |
| 6,049,421 A | 4/2000 | Raz et al. |
| 6,567,214 B2 | 5/2003 | Lorincz |
| 6,818,451 B2 | 11/2004 | Angros |
| 6,917,696 B2 | 7/2005 | Soenksen |
| 7,050,208 B2 | 5/2006 | Overbeck |
| 7,092,154 B2 | 8/2006 | Yasuda et al. |
| 2005/0112541 A1 | 5/2005 | Durack et al. |
| 2006/0055914 A1 | 3/2006 | Wojciechowski |
| 2006/0132878 A1 | 6/2006 | Curry et al. |
| 2006/0189893 A1 | 8/2006 | Maltzman et al. |

FOREIGN PATENT DOCUMENTS

| | | |
|---|---|---|
| WO | WO2005020244 | 3/2005 |

* cited by examiner

METHOD OF CONDENSED CELL SLIDE PREPARATION AND DETECTION OF RARELY OCCURRING CELLS ON MICROSCOPE SLIDES

CROSS-REFERENCE TO RELATED APPLICATIONS

This application claims priority under 35 U.S.C. § 119 to U.S. Provisional Patent Application No. 60/766,724, filed Feb. 8, 2006, herein incorporated by reference in its entirety.

GRANT REFERENCE

This invention was partially funded by NIH Contract No. 5R44CA104326-03. The government may have certain rights in the invention.

FIELD OF THE INVENTION

The present invention relates to the field of fluorescent detection of the rarely occurring cells in specially prepared densely populated microscope slide cell samples.

BACKGROUND OF THE INVENTION

There is a need in clinical cytology to detect, identify and analyze rarely occurring cells in the peripheral blood stream and various bodily fluids for diagnostic and research purposes.

One example of many such known procedures is extraction of rare fetal cells from the maternal blood stream for the purposes of clinical prenatal care. The fetal cells can cross the placental barrier and enter the maternal blood stream, from where they can be extracted by drawing a sample of the maternal blood and screening it for fetal cells of interest. This procedure is impeded by very low concentration of the fetal cells in the maternal blood stream, which is typically on the order of one fetal cell for tens of thousands of maternal blood cells.

Another example of such cytological procedures is detection of cancerous cells, which are disseminated in the blood stream from solid malignant tumors within the body, accessible only through invasive surgical procedures. The detection of occult tumor cells in peripheral blood is of crucial importance for early diagnosis of cancer as well as for cancer therapy monitoring and characterization of cancer type and stage, including remission as well as the potential relapse of the disease. To ensure cancer diagnosis at the earliest possible stage, it is essential to be able to detect very small numbers of tumor cells, e.g. down to the range of one tumor cell in one million to ten million non-tumor cells. To obtain a statistically significant number of cancer cells, it is necessary to sift out up to tens of millions of hematopoetic cells.

The tasks of detection of rarely occurring events on a conventional microscope slide carrier are not limited to the investigation of the blood samples for the above mentioned or similar purposes. The processes of screening of liquid and air-borne samples for bacteria, other pathogens and biological weapon agents can also greatly benefit from the convenience and efficiency of a microscope-based sample preparation and laser fluorescence scanning.

Genetic screening for gene alterations is still another procedure capable of being done with the above system. Examination of trisomy, monosomy, or specific targetable genes or genetic markers of identifiable defects (such as Down's syndrome or Tay-Sachs disease) could likewise benefit.

In spite of the multitude of various potential applications of the above-described development, the body of the current patent application will be focused on the specific implementation of the procedures for the preparation of the blood cell derived samples for the sake of clarity and consistency.

The tasks in the rare cell studies and other above-mentioned similar procedures are very demanding both with respect to the event detection technique and sample preparation methodology. Conventionally the rare cell detection is done by scanning the blood cells deposited on the microscope slide, rather than in the flow, in spite of the high sorting speed provided by flow cytometers. The slide deposition of the cells allows for convenient scanning, detection, identification, imaging and relocation of the rare cells for further analysis, as well as storage and archiving of the samples and information.

The preparation of the tens of millions cell samples on a single microscope slide requires deposition of cells on the microscope slide with very high density, approaching the ultimate limit density, and a high degree of utilization of the slide surface area, or else multiple slide preparations would be required to analyze the single blood sample.

The state of the art in microscope slide based cell preparation involves different types of leukapheresis procedures, most commonly based on centrifugation, which separate white blood cells and, similar to them and inseparable by physical characteristics, rare cells of interest from other constituents of the whole blood, like the red blood cells, platelets and plasma.

Not every one of the existing microscope slide based cell preparation procedures seems to be acceptable for rare cell detection. For example, regular cytospin preparations can result in a loss of many (e.g. up to $2/3$) of the cells.

An example of more efficient cell sample preparation for microscopic analysis ("Detection and Analysis of Cancer Cells in Blood and Bone Marrow Using a Rare Event Imaging System", Clinical Cancer Research, Vol. 6, 434-442, February 2000) relies on the attachment of live cells to specialized adhesive slides (Paul Marienfeld GmbH & Co., KG, Bad Mergentheim, Germany) in three circular wells, 15 mm diameter each. This procedure is complicated not only by the necessity to deposit live cells, but also by the multi-step processes of fluorescent immunocytochemical staining and washing, which all have to be performed on the slide containing the attached cells. It takes half a day to prepare a slide sample following the aforementioned procedure, which is not prone to automation. Additional drawbacks of this procedure are high cost of the custom-designed slides and low (e.g. only 27%) level of utilization of the slide surface area. With moderate average cell density of 200,000 cells/$cm^2$ only about 1 million cells could be analyzed per slide, requiring multiple slide preparations for multi-million cell screening from the single blood sample.

Microscope slide samples prepared by the aforementioned procedure were subsequently analyzed by an automated digital microscope based fluorescent image analysis system. Inherent limitations of a microscope-based system include tiny field of view and a limited brightness mercury light source and a CCD camera requiring long integration time which resulted in slow frame by frame slide scanning speed, which in turn lead to about one hour of scanning time for one slide.

Other approaches utilize extreme spectral brightness of a laser light source to increase fluorescence excitation intensity and high sensitive photo-multiplying tube (PMT) based detectors to accelerate the fluorescence data acquisition rate. Straight forward translational scanning employed, for example, in commercial GenePix Scanner (Axon Instruments, Inc.) encounters inertial limitations to the scanning speed from the bulky translation stages.

The laser excitation beam can be swept by a galvanometer-actuated mirror scanner. ("Detection and Quantification of Small Number of Circulating Tumor Cells in Peripheral Blood using Laser Scanning Cytometer (LSC®)" Clin Chem Lab Med, Vol. 39, 811-817, 2001). This instrument scans the laser spot within the tiny field of view of the microscope objective lens, which produces high spatial resolution, but at the expense of slow overall scanning speed, allowing for the analysis of only 50,000 cells in 30 min.

Significant acceleration of scanning speed was achieved by increasing the galvanometric sweeping range of the excitation laser spot up to the full 50 mm width of the microscope slide ("A Rare-Cell Detector for Cancer", PNAS, Vol. 101, No. 29, 10501-10504, Jul. 20, 2004). The combination of fast (100 scans per second) galvanometric sweeping and 2 mm/sec translation resulted in surface scanning speed of 1 $cm^2$/sec and allowed to pre-scan 25 $cm^2$ slide area for rarely occurring occult tumor cells at the scan rate of 400,000 peripheral blood cells per second. The fluorescence emission was collected by a straight portion of a linear-to-circular fiber optic aperture transformer placed close to the swept laser spot. The filtering aperture is grossly under-utilized in this case, since only a few of the optical fibers in the linear bundle are collecting the fluorescent light at a time and deliver it to the circular bundle. This drawback implicates the usage of a multi-lens collimating optical system, jeopardizes pass band and stop band characteristics of oversized optical fluorescence emission filters, and requires an oversized PMT photocathode. An additional disadvantage of galvanometric mirror sweeping is deviation from linearity of the combination of galvanometer and F-Theta scanning lens, which produces significant beam position distortion.

To implement a successful, cost effective, and widespread system for detection of rarely occurring cells, there are needs for both the efficient and automatable cell deposition on a microscope slide and a fast, simple, and reliable fluorescence detection technique.

BRIEF SUMMARY OF THE INVENTION

In accordance with one aspect of the present invention, highly condensed cell slide samples are prepared. The concentrated suspension of immunocytochemically stained cells is mixed with liquid gel solution. The mixture is dispensed on the surface of the bordered microscope and sealed under protective cover slip. The density of the resulting homogeneous monolayer of cells in thin layer of hardened gel exceeds 2 millions cells per $cm^2$. In accordance with another aspect of the present invention, the rarely occurring cells are detected on the multiple slides placed on a rotating and radially translated turntable. Fluorescence excitation is optimized by pointing an elliptically shaped laser spot on the slides at an angle exceeding the angular aperture of the fluorescence collecting objective lens. High fluorescence collection efficiency by a high numerical aperture aspheric objective lens allows for fast and efficient detection of rare fluorescing cells on the scanned microscope slides with reduced laser power. As a result of the combined new methods of efficient condensed cell deposition and fast and simple laser excitation and fluorescence detection, pre-scanning of the cell samples on the microscope slide can be done at the rate exceeding 2 million cells per second.

According to another aspect of the present invention, a method of detection of a rarely occurring event within one or more biological samples is provided. The method includes (a) processing each biological sample to provide a gellable liquid solution comprising concentrated biological sample and a flourochrome designed to associate with a rarely occurring event within the concentrated biological sample; (b) depositing the solution in a layer on a surface of a slide; and (c) scanning the solution on the slide with energy adapted to cause fluorescence of the flourochrome to detect potential instances of the rarely occurring event within the concentrated biological sample in the solution. The method may further include analyzing the potential instances of the rarely occurring event to filter out potential instances of the rarely occurring event from not actual instances of the rarely occurring event as well as maintaining location information for potential instances of rarely occurring events.

According to another aspect of the present invention, a method for detection of a rarely occurring event within one or more biological samples is provided. The method includes processing each biological sample to provide a concentrated sample, depositing a concentrated sample in a gellable liquid solution on each of a plurality of slides, mounting the plurality of slides on a rotatable turntable in precisely identified locations, prescanning the plurality of slides using laser fluorescence excitation and collection to determine potential instances of the rarely occurring event within the concentrated sample, analyzing the potential instances of the rarely occurring event to filter out potential instances of the rarely occurring event from not actual instances of the rarely occurring event, maintaining location information for remaining potential instances of the rarely occurring event, using the location identification information to locate the potential instances of the rarely occurring event for additional analysis, and providing the additional analysis to detect instances of the rarely occurring event from the remaining potential instances. The rotatable turntable may be rotating during the prescanning and may be rotating while linearly translating to thereby provide for a spiral path of travel of the scan relative to the slides.

According to another aspect of the present invention a condensed cell slide preparation apparatus includes a slide having a surface and a raised border around the surface defining a volume above the surface adapted to hold a gellable solution of cells. There is at least one channel through the raised border.

According to another aspect of the present invention, an apparatus for detection of a rarely occurring event with a biological sample is provided. The apparatus includes a laser adapted to produce a laser beam to generate fluorescence related to the rarely occurring event, a linear translation stage comprising a carriage and actuator, the actuator adapted to move the carriage along a linear path, a turntable mounted on the carriage of the linear translation stage, the turntable having a motor to rotate the turntable and a plurality of slides at spaced apart locations around the turntable. Each slide is adapted to carry a biological sample. The linear translation stage and turntable are adapted to concurrently operate to pass the plurality of slides through the laser beam in a spiral pattern. There is also a laser fluorescence collection device adapted to collect any laser-induced fluorescence.

According to another aspect of the present invention, a system for detection of a rarely occurring event within a biological sample is provided. The system includes an automated cell dispensing tool for dispensing cells from the biological sample on microscope slides, a computer-controlled system for detection of rarely occurring cells on microscope slides using laser excited fluorescence collection, and a device for providing additional analysis of cells detected using the laser excited fluorescence collection.

DETAILED DESCRIPTION OF THE EXEMPLARY EMBODIMENTS

A detailed description of exemplary embodiments is provided to assist in explanation of the present invention. This description is not intended to limit the invention only to the specific embodiments described in detail.

The present invention provides for detection of rarely occurring events within biological samples. Of particular interest is detection of diseases, including cancereous cells in the blood stream, but other events may be of interest in other types of cells. The present invention provides for the detection of rarely occurring events within biological samples in a manner that may be performed quickly with high throughput using automated processes. For purposes of explanation, the condensed cell slide preparation aspect of the invention is discussed first followed by the fluorescent detection of rarely occurring cells on the microscope slide.

Condensed Cell Slide Preparation

As a first step in the preparation of densely populated microscope slides according to an exemplary embodiment of the present invention, a mixture of rare cells with white blood cells must be extracted from whole blood following standard leukapheresis procedures, most commonly based on multiple processes of centrifugation of cell suspension in a liquid carrier, such as phosphate buffered saline (PBS), followed by re-suspension of the pelleted cells.

These and all the following cell-handling processes are preferred to be executed in a liquid suspension, a cell's natural environment, rather than after attachment of the cells to the surface of the microscope slide, as it was done in the aforementioned example of the state of the art.

Hence, all the subsequent fluorescent immunocytochemical staining procedures are conveniently performed on the cells in test tubes and in liquid suspension. This makes the process of cell preparation easily automatable by making it possible to utilize the potential of existing commercially available robotic liquid handling systems.

Briefly, cells from a sample are lightly fixed, rinsed in an appropriate buffer, blocked to alleviate nonspecific binding of proteins, and then stained with fluorochrome anti-bodies directed against surface markers specific for the rare cell types being tested. In some cases, primary antibodies may not contain a fluorochrome tag and a secondary fluorochrome tagged antibody will be used, to increase the signal-to-noise ratio. After antibody staining, the cells are rinsed, concentrated, and placed into a gel or hydrogel material such as a fibrin matrix. Cells are then ready to be dispensed at high concentration onto the slides. Addition of antifading compounds, such as O-phenylenediamine, may be included to the gel or hydrogel materials to help prevent fluorescent fading.

The pre-deposition tagging process reduces the total time for sample processing and allows the slide chamber cover slip to be put in place and sealed immediately after the deposition process is complete. The change in normal process protocol is a significant step forward for the rare event detection process in that the total sample processing time has been reduced and the lack of post-deposition slide processes reduces the sample contamination that is often responsible for false positive readings.

The final step of the deposition of the cells on the microscope slide can also benefit from easily implementable automated dispensing of liquid suspended cells. A microliter range amount of liquid cell suspension can be precisely spread over the surface of the bordered microscope slide area either by rastering it with a circular orifice or by sweeping it with a slotted orifice of an automatic cell dispensing tool such as are known in the art.

It is advantageous for the liquid cell carrying medium to be not of the plain water-based nature, which would dry out on the surface of the slide and leave the cells exposed, but of gelatable, (preferably bio-) polymerizable nature instead. This would allow for a more controllable process of deposition of a compact and homogeneous monolayer of cells mounted within the polymerized matrix. Moreover, the process of automated deposition of cell impregnated matrix layers can be repeated many times, producing a homogeneous, three-dimensional multilayer structure capable of containing the amount of cells many times exceeding the ultimate tight surface packing limit.

There are several materials which can execute the desirable functions of the cell carrying matrix. Among them are numerous hydrogels, both natural and synthetic. They are cell friendly and biocompatible materials and exhibit good optical quality.

An example of a natural hydrogel is collagen, a natural component of ligaments, cartilage and extracellular matrix in the body. Collagen demonstrates adequate hardness at low concentration in watery solutions (2-4% w/w); it can support high viability of the deposited cells. Collagen compounds are normally liquid at temperatures close to 0° C., and turn to gel upon increasing temperature to the ambient level. Therefore, cells mixed with collagen can be deposited onto pre-cooled slides via a chilled deposition head, followed by incubation of the slide at room temperature or at 37° C. in high humidity, to prevent dehydration. Collagen is transparent and optically homogeneous, thus making excellent slide material.

Poloxamers, such as Pluronic F-127, copolymers of polyethylene oxide and polypropylene oxide blocks, may demonstrate inverse temperature gelation similar to that of collagen. Pluronic F-127 at 20%-35% in water is liquid at 0° C.-6° C. and congeals at ambient temperature. Pluronic F-127 is widely used in cell culturing, and therefore is a promising material for high density cell slides.

Another material which can be selected as a universal adhesive and carrier for high density cell deposition is fibrin gel. Fibrin gel is a natural component of blood clots preventing hemorrhage after physical damage of the blood system. Specially formulated and highly concentrated, it is widely used as surgical glue (known as "Fibrin Glue") throughout the world. The ordinary formulation includes fibrinogen and thrombin counterparts as well as calcium and anti-degradation additives.

Fibrin gel is an entirely cell-friendly medium leaving cell surface and morphology undisturbed. Applied as is, fibrin glue has excellent adhesive properties yet looks very much opaque, and hence optically impertinent for the epifluorescent slides. Optical properties of fibrin glue are very much improved if fibrinogen solution (concentration ~5 mg/ml) is deprived of calcium and buffer components and maintained in 0.1% NaCl solution at pH 6.8. Fibrin gel still retains much of its adhesive properties, but markedly reduces its turbidity, thus becoming a very good optical non-fluorescing cell containing matrix. A small volume of fibrinogen solution is added to and mixed with the same amount of high concentration cell suspension shortly before the deposition.

Figure 1A:
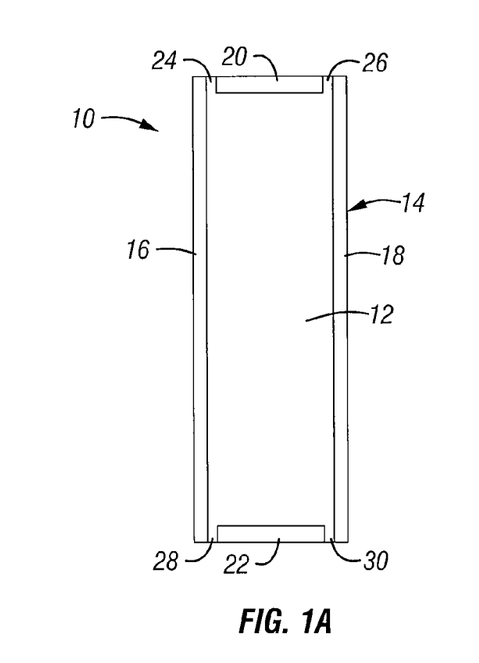
FIG. 1A is a top view of a microscope slide with a bordered perimeter according to one aspect of the present invention.
Figure 1B:
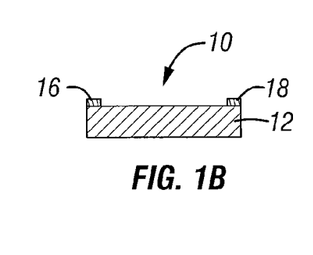
FIG. 1B is a cross sectional view of the microscope slide of FIG. 1A.
Figure 1C:
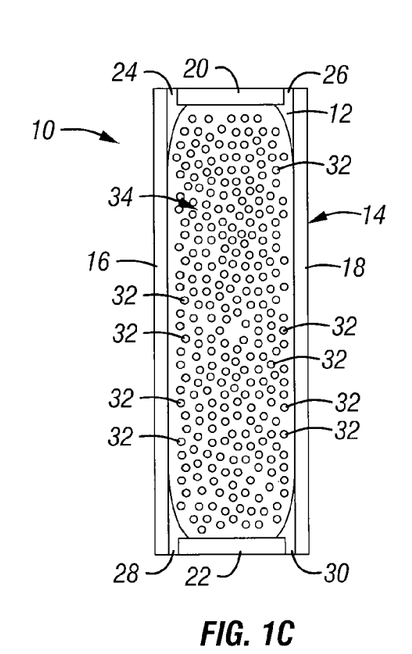
FIG. 1C is a top view of a microscope slide with a bordered perimeter and having cells suspended in a liquid gel solution according to one aspect of the present invention.
Figure 1D:
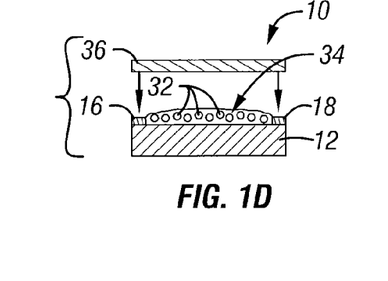
FIG. 1D is a cross sectional view of the microscope slide with cells suspended in the liquid solution of FIG. 1C.

The deposition of the cells suspended in the gel matrix is performed on standard microscope slides modified to confine the cell suspension as shown in FIGS. 1A-1F. For the purposes of confinement of the cell suspension within the limits of the microscope slide surface 12, the standard slides are provided with shallow (approximately 30 µm high) framing border spacers 16, 18, 20, 22 at the perimeter of the slide 10 as shown in FIG. 1A. The border frame 14 on the slide 10 also doubles as a spacer for the protective microscope slide cover 36. The framing border spacers 16, 18, 20, 22 can be either adhered to, screen printed or directly written on the surface 12 of the slide 10, allowing slides to be prepared in mass quantities while adding only a few cents to the overall costs of the individual slides.

For deposition of the cells suspended in natural (collagen) or synthetic (poloxamer) hydrogels with inverse temperature gelation, both cell containing gel solution and microscope slide substrate have to be chilled to close to 0° C. for the gels to stay liquid.

To the contrary, the deposition and gelation of the fibrin can occur at normal temperature with the assistance of a thrombin counterpart, a specific enzyme initiating the cleavage and cross-linking of fibrinogen. For this purpose the surface of the microscope slide is pre-treated with thrombin. A small volume (50 µl) of low concentration (~1 mg/ml) solution of thrombin is deposited on optical surfaces of the slides, and then dehydrated.

Figure 1E:
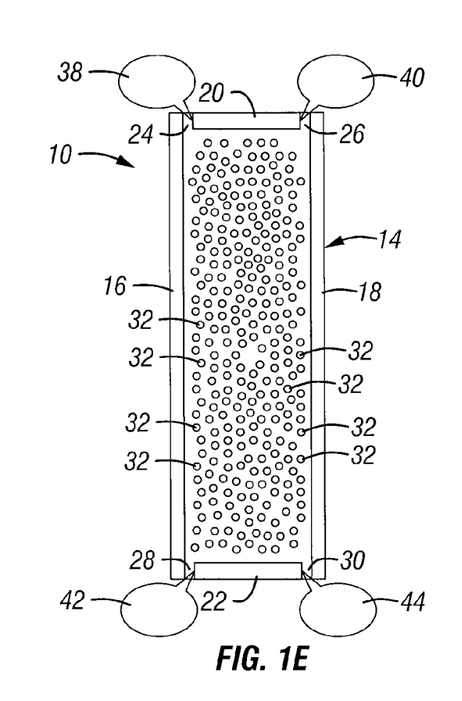
FIG. 1E is a top view of a microscope slide showing excessive liquid gel solution overflow with a slide cover in place according to one aspect of the present invention.
Figure 1F:
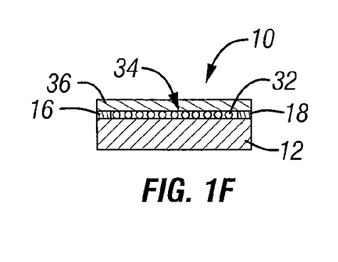
FIG. 1F is a cross sectional view of the microscope slide of FIG. 1E.

After deposition of 60 µl of properly concentrated cells 32 suspended in liquid gel solution 34 on the surface 12 of the slide 10 (FIG. 1C), the protective glass cover 36 (FIG. 1D) is placed on top of the slide 10 before the gel 34 sets, extruding the excessive gel solution 38, 40, 42, 44 through the provided drainage channels 24, 26, 28, 30 (FIG. 1E). The final setting of the gel 34 is delayed, this providing sufficient time for cells to settle on the surface 12 of the slide and form a compact and homogeneous monolayer in the thin liquid layer of gel matrix. Afterwards the cogelation of the hydrogels is induced by elevating the temperature of the slides to ambient for poloxamer and to 37° C. for collagen. The setting of the fibrin gel is induced by thrombin gradually dissolving back into fluid and slowly starting the enzymatic process of gelation. Finally, the edges of the cover glass 36 are sealed with sealant, for example, nail polish (not shown), thus forming high quality optical slides suitable for imaging and storage. Sealant around the edges could also be used to prevent the slide from drying out.

The implementation of the aforementioned procedure of condensed cell slide preparation produced microscope slides with cell density in excess of 2 million cells per square centimeter, half of the ultimate density limit for the tightly packed 5 µm diameter cells, leaving only half of their size worth of elbow room between the adjacent cells. The total number of cells deposited with this density on the bordered slide with 75% utilized surface area exceeds 28 millions cells per slide.

Fluorescent Detection of Rarely Occurring Cells on the Microscope Slide.

Fast and efficient fluorescence-based detection of the rarely occurring cells on the microscope slide relies on optimum execution of both its constituting parts: excitation of the fluorescence and collection of the fluorescent light. Having high spectral brightness and perfect spatial coherence, lasers long ago became the light source of choice for efficient fluorescence excitation.

Figure 2:
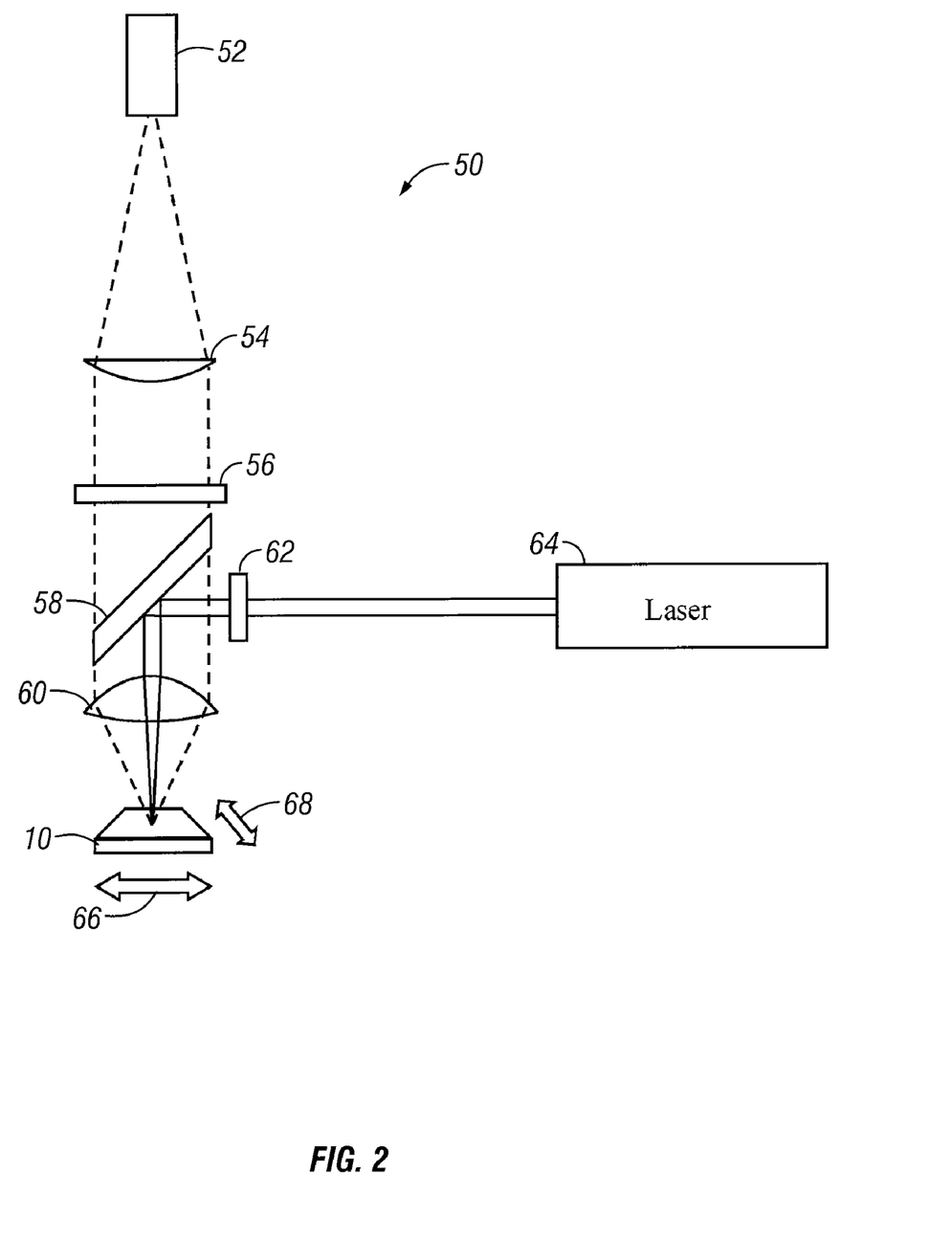
FIG. 2 is a schematic diagram of a laser excited epifluorescence collection and detection system for a scanned microscope slide according to an aspect of the present invention.
Figure 3:
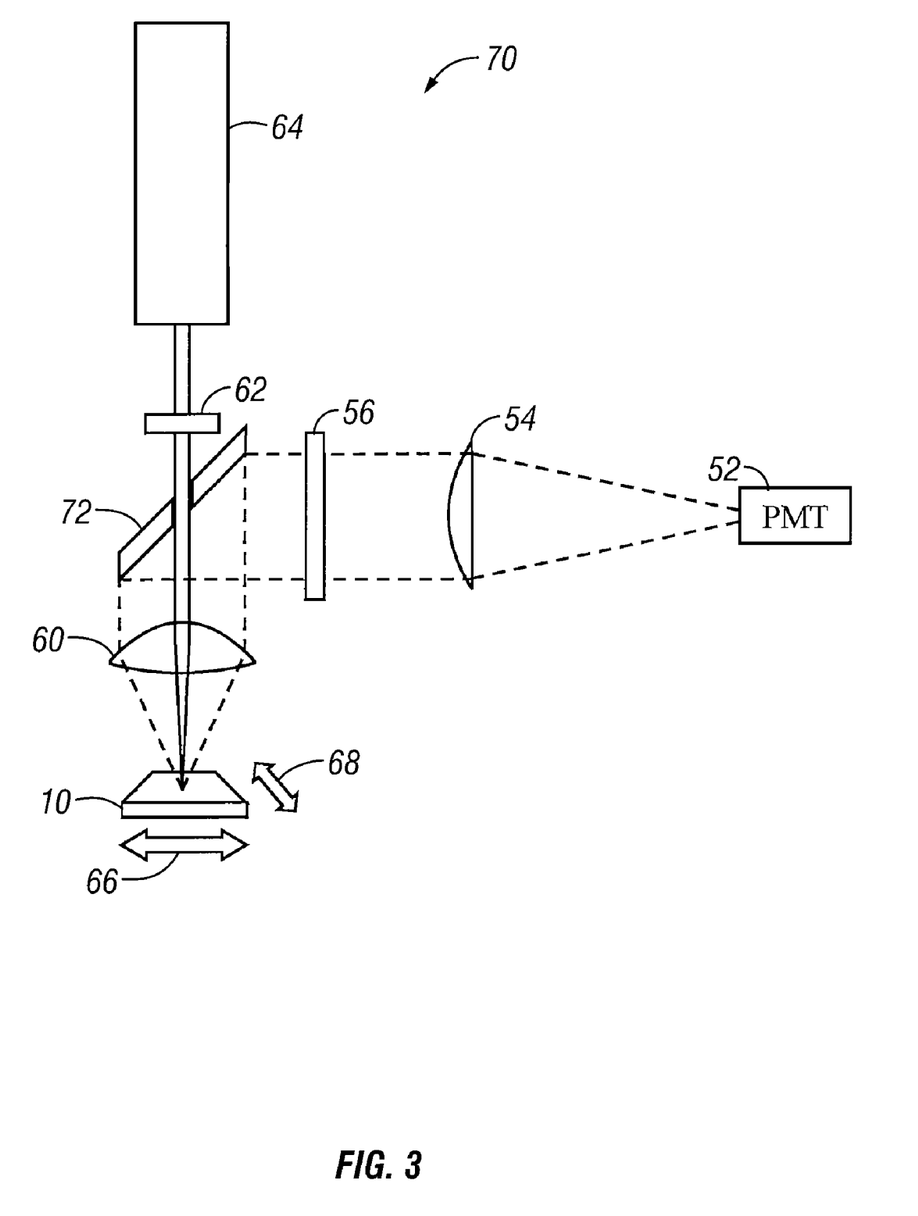
FIG. 3 is a schematic diagram of a laser excited fluorescence collection and detection system for a scanned microscope slide, having a beam splitting mirror with a small hole in place of the dichroic beam splitting mirror according to an aspect of the present invention.
Figure 4:
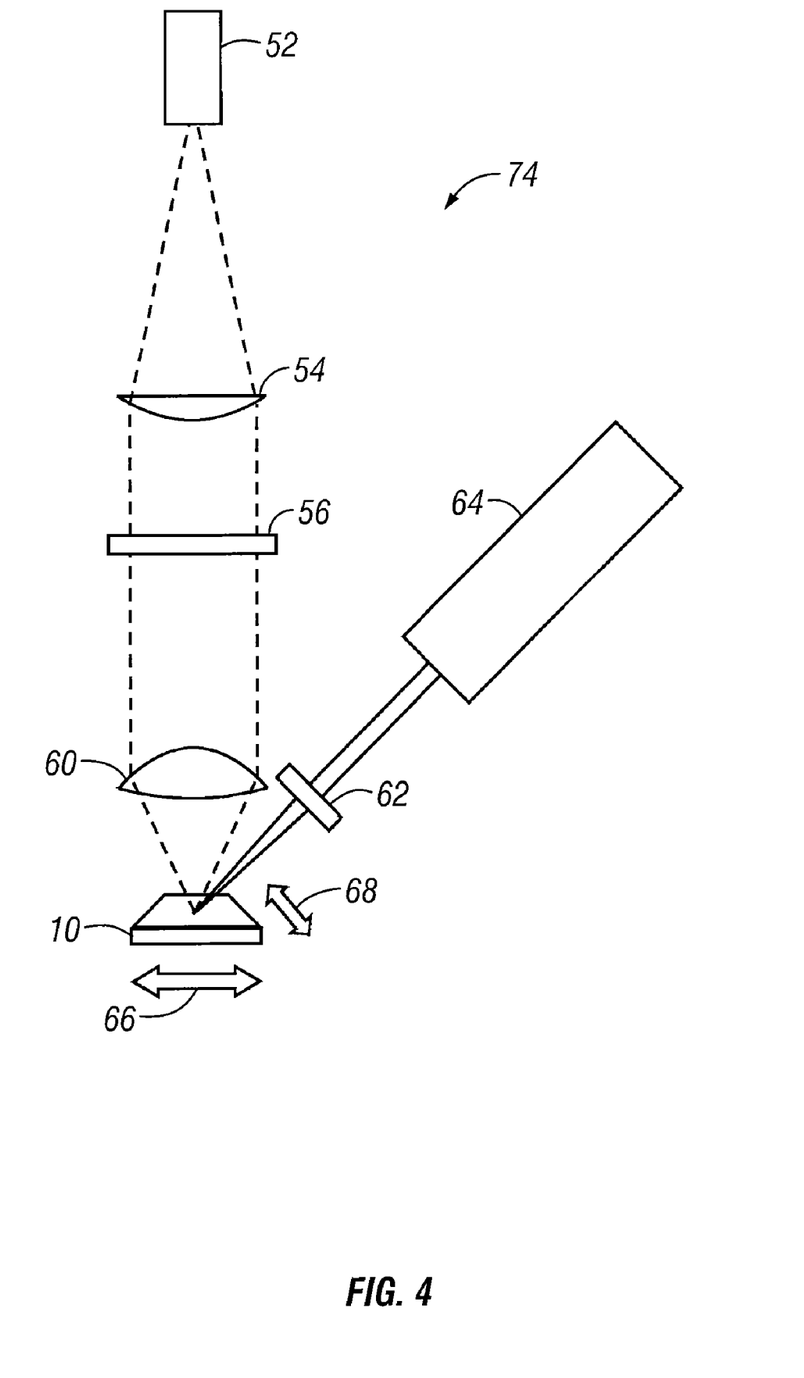
FIG. 4 is a schematic diagram of a beamsplitterless fluorescence excitation and fluorescence collection and detection system with oblique incidence of a laser excitation beam on the surface of the scanned microscope slide according to an aspect of the present invention.

Various embodiments of laser fluorescence excitation are depicted in FIGS. 2-4. Most commonly, the laser beam from laser 64 is directed to an objective lens 60 by a dichroic beam splitter mirror 58 and tightly focused by the objective lens 60 on the surface of the scanned slide as shown in FIG. 2. Additional anamorphic optics (usually comprised of cylindrical lenses), also referred to as laser spot forming optics 62, is used for laser spot forming. XY scanning occurs along the x-axis 66 and the y-axis 68.

Fluorescence, excited by the highly intense focused laser beam, is collected by the objective lens 60, collimated, passed through the dichroic beam splitting mirror 58, filtered out of the scattered laser light by emission filter 56, which can be a combination of band pass and long wave pass filters, and finally focused (see 54) on the photocathode of the photomultiplier tube or PMT 52.

Different embodiments, as in FIG. 3, may have a mirror with small hole 72 in place of the dichroic beam splitter mirror 58, exploiting tight collimation of a spatially coherent laser beam for more efficient separation of the laser excitation beam and fluorescent light.

To reduce the optical losses and the residual leakage of the scattered and reflected laser light even further, a beam splitter can be eliminated altogether (FIG. 4) by pointing the focused laser excitation beam on the scanned slide 10 from outside of the angular aperture of the objective lens 60 at an oblique angle, preferably close to the Brewster angle, advantageously zeroing out any reflections of the laser beam linearly polarized in the plane of incidence. Another benefit of the oblique angled laser excitation of the fluorescence depicted in FIG. 4 comes from fact that the passing laser beam, by the time it hits the opposite side of the slide, becomes offset far enough to move beyond the field of view of the fluorescence collecting optics, thus eliminating the detection of any fluorescence from debris and contaminants on the opposite side of the slide.

The collection efficiency of the fluorescent light depends on the numerical aperture of the objective lens and increases as a second power of it. For this purpose a high (>0.6) numerical aperture single element aspheric objective lens can be successfully utilized. High quality imaging properties are not essential in this case, so even low cost molded glass aspherics would not jeopardize spatial resolution. Spatial resolution is determined by the size of the focused laser beam, not by image distortion of the full aperture aspheric lens. The laser beam, when focused through the aspheric objective lens 60 in the embodiments in FIG. 2 and FIG. 3, is minimally distorted by non-ideality of the molded aspherics by virtue of the insignificantly small portion of the total aperture of the aspheric objective lens it occupies. Spatial resolution of the beamsplitterless embodiment in FIG. 4 is especially immune to imperfections of the aspheric objective lens because the incident laser beam is not passing through it, but instead is focused by dedicated low numerical aperture spot forming optics alone.

Each of the embodiments of the laser excited fluorescence collection system 50 shown in FIG. 2, the system 70 of FIG. 3, and the system 74 of FIG. 4 may have additional fluorescence selection channels incorporated in the main fluorescence collection path by means of fluorescence splitting dichroic mirrors and separate emission filters and detectors (not shown for simplicity). Additional channels allow for the detection of the fluorescence emitted by different fluorochromes excited by the same laser source.

Figure 5:
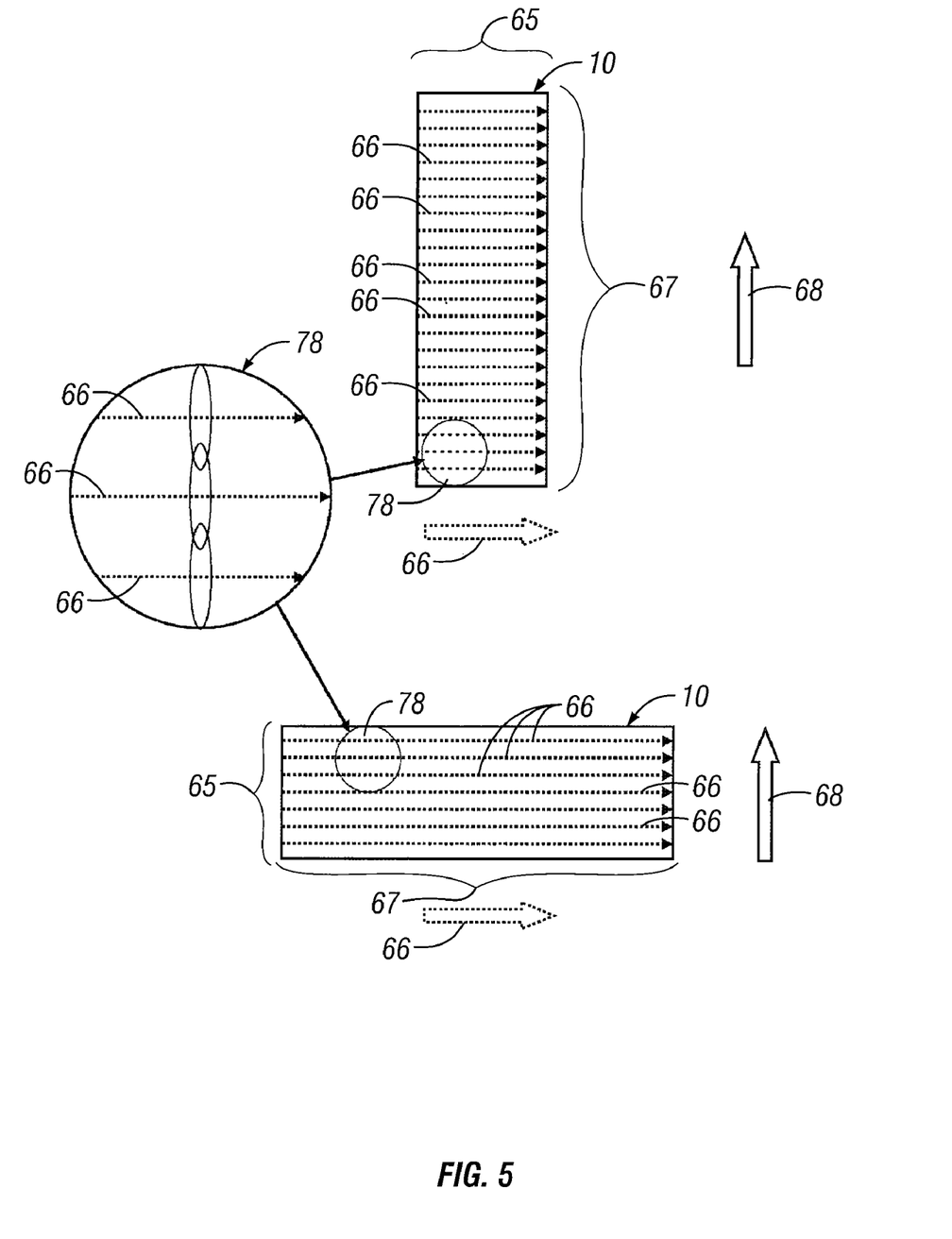
FIG. 5 is an illustration of the scanning patterns for microscope slides being scanned in short and long directions by an elliptically shaped focused laser spot according to an aspect of the present invention.

In FIG. 5, fast sweeping of the surface of the microscope slide 10 is illustrated by dotted arrows 66. The fast sweeping may be performed either in the direction of the short 65 or long 67 dimension of the microscope slide, while the slow linear translation of the slide 10 is in correspondingly perpendicular direction, as indicated by solid arrows 68 in FIG. 5. The insert 78 (the enlarged isolated view) in FIG. 5 illustrates the elliptical shape of an anamorphically focused laser beam. The laser spot is tightly focused down to 10-20 µm in the direction of the fast sweep to produce high enough resolution of comparatively small cells. The width of the laser spot in the direction perpendicular to the direction of the fast sweep is made at least 100 µm to ensure wide surface coverage by overlapping laser beams, as illustrated in the insert 78 in FIG. 5. The 100 µm wide elliptical focused laser beam can scan 1 square centimeter per second if swept at the speed of 1 m/sec. This scanning rate allows for the full area of the standard 1"×3" microscope slide to be scanned in under 20 seconds.

Summarizing, with above mentioned surface cell density in excess of 2 million cells per square centimeter in mind, a scanning rate higher than 2 million cells per second can be achieved as a combined result of the new condensed cell deposition method and fast and efficient fluorescence excitation and detection technique.

As it was already mentioned above, 1 m/sec and higher scanning speeds are very challenging for linear reciprocating translation stages because their inertial properties severely limit the rate of rapid accelerations and decelerations. Less inertial galvanometer based systems are able to sweep at high rates, but have limited aperture and significant distortion of the scanning linearity.

Figure 6:
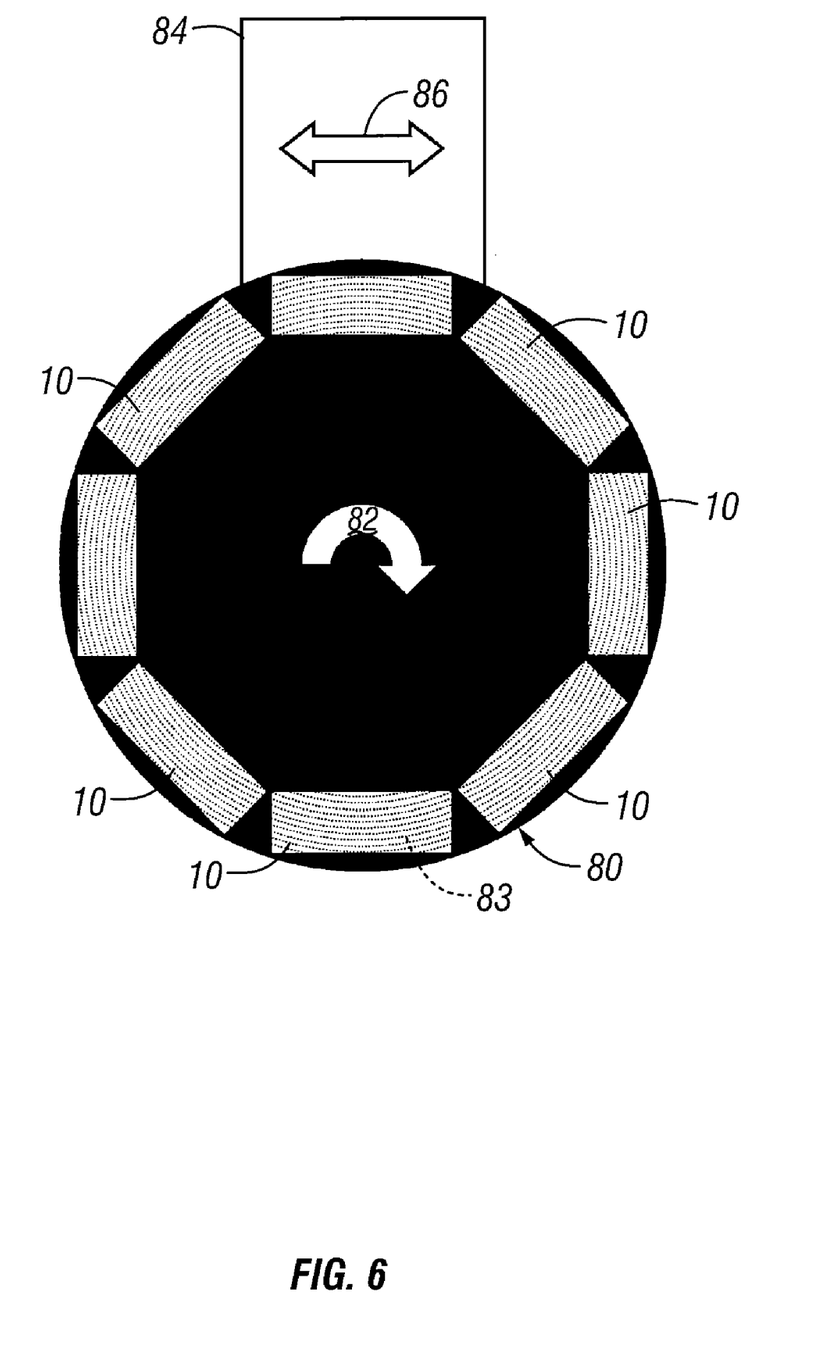
FIG. 6 is a representation of multiple microscope slides arranged in a ring on a rotating turntable mounted on linearly translating stage according to an aspect of the present invention.

The problem of rapid accelerations and decelerations can be eliminated if the swept samples keep moving at constant speed, for example, circularly, as indicated by arrow 86 as shown in FIG. 6, where multiple microscope slides 10 are mounted in a ring fashion on a rotating turntable 80, with the arrow 82 indicating the direction of rotation. The linear speed in excess of 1 m/sec can be achieved by rotation at a moderate rate of 100 rpm and at a 10 cm distance from the rotation axis. The related centrifugal acceleration of about 1 g will not pose any danger for the cells securely mounted in the polymerized gel. This arrangement allows for mounting of a plurality (eight as shown) standard microscope slides 10 in a ring fashion at the perimeter of the turntable 80. It allows one to either increase drastically the number of cells analyzed from the single blood sample, or to analyze multiple cell preparations from different blood samples simultaneously.

Scanning the fluorescing rare cells with a 10-20 µm focused laser beam at 1 m/sec generates the moderate requirement for a signal bandwidth under 1 MHz. This fact allows one to increase the transimpedance and, correspondingly, the detected signal gain of the PMT tenfold with respect to the state of the art ("A Rare-Cell Detector for Cancer", PNAS, Vol. 101, no. 29, 10501-10504, Jul. 20, 2004), incorporated by reference herein. As a result, the laser power can be decreased from tens to a few milliwatts, reducing the system complexity, cost and risk of photobleaching of the fluorochromes.

Overall raster scanning of up to eight microscope slides 10 mounted on the turntable 80 can be achieved by slow radial translation of the rotating turntable by means of a linear translation stage 84 in the direction indicated by the arrow 86 in FIG. 6. The resulting spiral scan trace 83 is shown by dotted lines and assumes a shape close to circular arches on the surface of every individual scanned slide 10. With a 28 million cells per slide deposition density achievable as described previously, eight slides mounted on the turntable have provided the capacity to scan 224 millions cells in a single run. In case of a three-dimensional multilayer cell-containing structure, the total number of the scanned cells increases with the number of layers and can reach up to 1 billion cells per run for just four layer cell deposition. Of course, the present invention contemplates additional layers.

Loading of individual slides 10 is accomplished by lowering and then securely clamping them against precise reference stops in their separate holding places either manually or by robotic manipulator, one slide 10 per each 45 degree turn of the turntable 80, as in case of eight slides arranged in a 10 cm radius ring. Alternatively, operations of loading and unloading of the slides 10 can be segregated from scanning by utilizing a designated disk shaped slide holding cassette, in which slides can be loaded or unloaded at a separate station. The slide holding cassette is easily and quickly placed in a keyed and locked position on the turntable 80. The cassette with already pre-scanned slides can be promptly replaced with the new one. The slides can be left in their respective places on the slide holding cassette for the following step of detailed evaluation of detected rare cells under an automated digital microscope, providing that the microscope is equipped with a similar turntable and linear translation stage.

Figure 7:
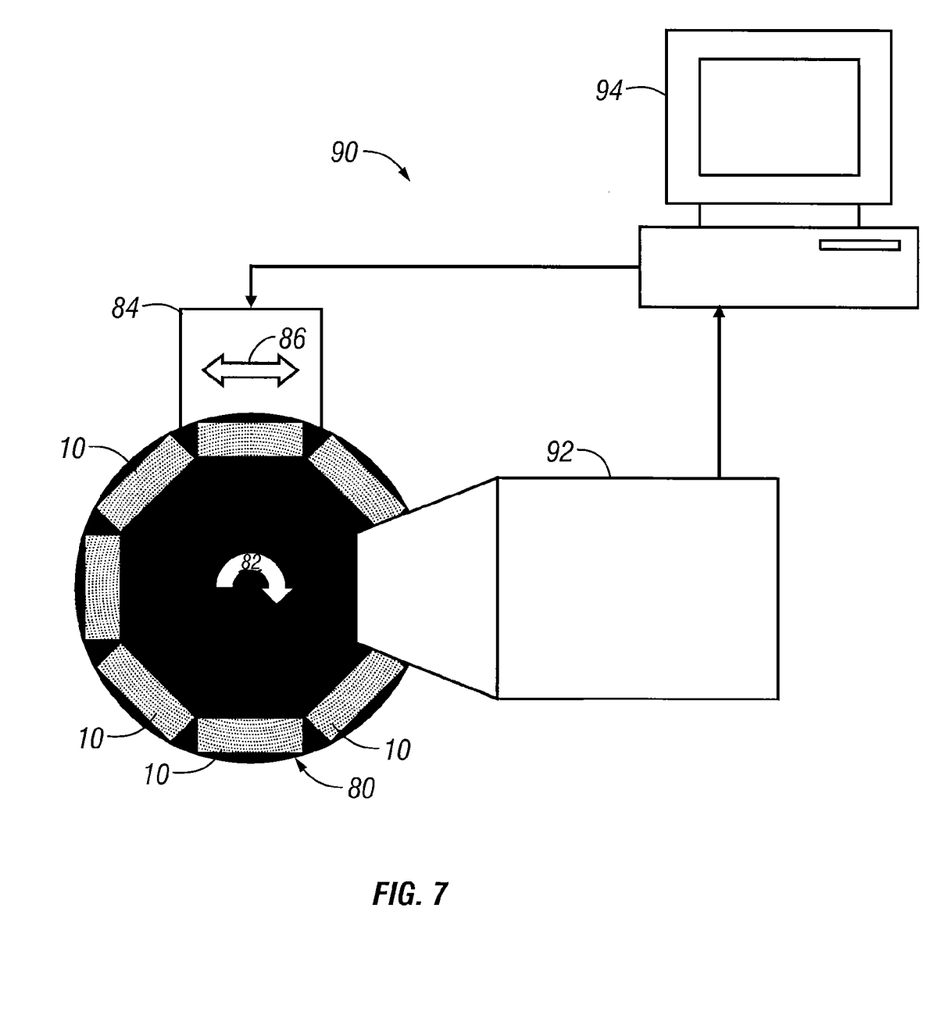
FIG. 7 is a diagram of a computer-controlled system for detection of rare cells deposited on microscope slides placed on a spinning and linearly translated turntable with single laser excitation and fluorescence detection detailed in FIGS. 2-4.

FIG. 7 illustrates a computer-controlled system 90 for detection of rarely occurring cells on microscope slides by means of laser excited fluorescence collection 92 according to an exemplary embodiment of the invention. Both linear translation of the turntable 80 and its rotation are performed by computer-controlled stepper motors with optical encoders controlled by computer 94 to ensure the precise acquisition of the coordinates corresponding to every data point of detected and digitized collected fluorescence intensity. Strict referencing of the recorded and stored coordinates and fluorescence intensity data to the actual position of the detected fluorescing rare cells on the surface of the microscope slide can be achieved both passively by securing the slides against precise alignment stops and actively, by fluorescently marking the edges of the corners of the scanned microscope slides to generate self-referencing data points embedded within the domain of the detected and digitized fluorescence signal.

Pre-scanning of the microscope slides 10 for the rarely occurring fluorescent cells can be arranged both in the up-right configuration, when laser fluorescence excitation and fluorescence collection and detection are accomplished from the top, as it is depicted in FIGS. 2-4, and in the inverted configuration, when laser fluorescence excitation and fluorescence collection and detection are accomplished from below. In both configurations, microscope slides can be placed with the cell-covered side facing up or down, correspondingly, cells can be deposited either on the front or on the back surface of the slide, depending on the configuration. Placing the slides face-up in an up-right configuration and face-down in an inverted configuration eliminates the opposite surface of the microscope slide from the optical path of the fluorescent light being collected. An additional advantage of the inverted configuration with face-down placement of the slides is reduced contamination of the slides by airborne dust and particulates.

In case of a three-dimensional cell-containing structure being built on the microscope slide by repeated deposition of multiple monolayers of cells, as was previously discussed, the efficiency of laser excitation and fluorescence collection will not be impaired, because of little distortion of the mildly focused laser beam and negligible blockage of the fluorescent light produced by the transparent, only slightly scattering overlaying cells. This would not prevent detection of the rare fluorescent cells within the three-dimensional structure any less reliably than in the monolayer, except for the depth of the cell location within the multi-layer structure. The lack of the depth coordinate of the detected cells does not constitute any drawback of the multilayer cell deposition. Final and refined inspection of detailed structure and morphology of the detected cells of the multi-layer structure can be performed under epi-fluorescent or, if necessary, under a confocal fluorescent microscope.

Post-scanning data analysis, including filtering out false positive signals from dust and debris particles, provides the coordinates of the detected-during-pre-scan rare cells on the microscope slides, allowing for the re-location of the detected rare cells for further detailed analysis with an automated digital epi-fluorescence microscope system.

Figure 8:
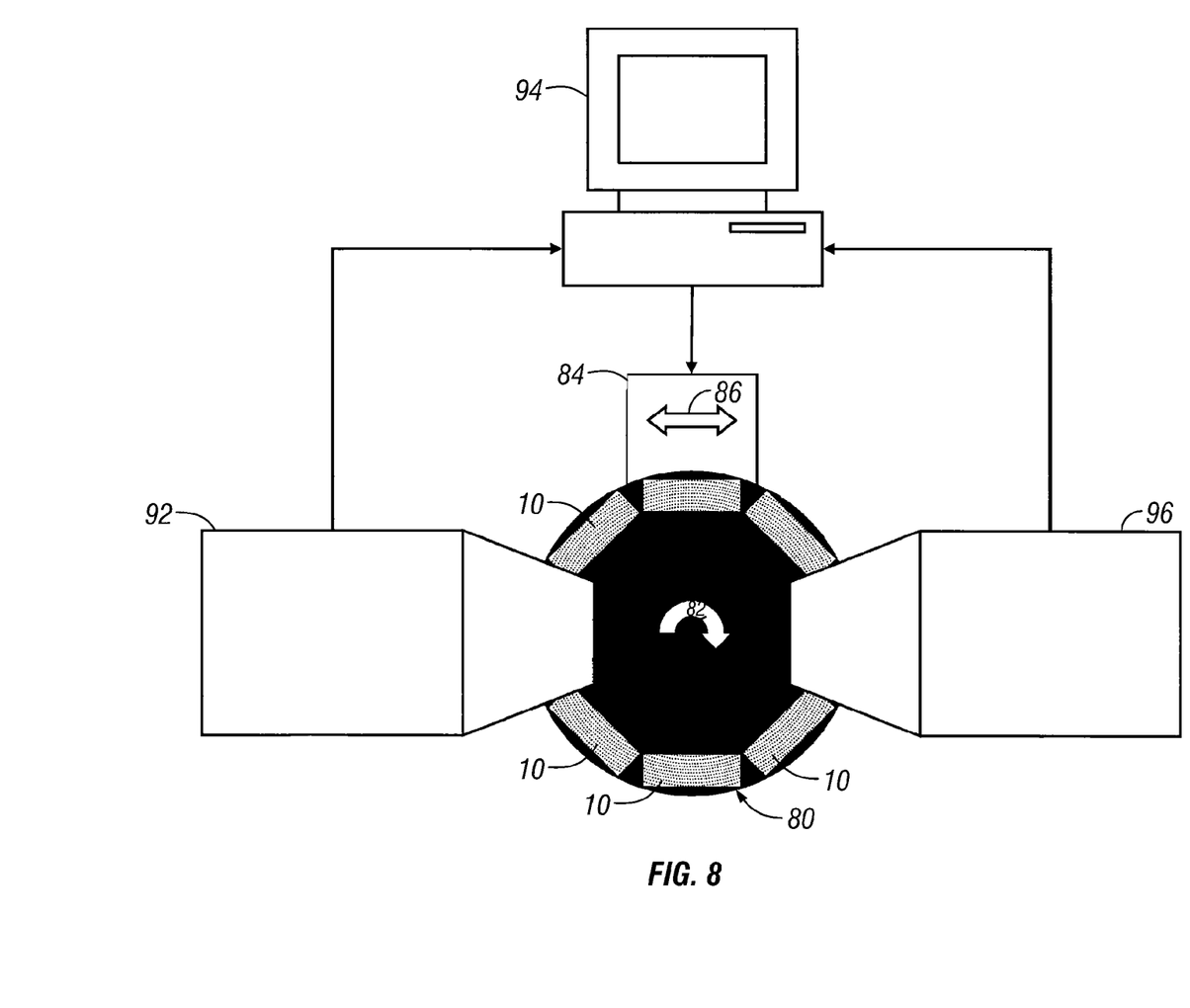
FIG. 8 is a diagram of a computer-controlled system for detection of rare cells deposited on microscope slides placed on the spinning and linearly translated turntable with dual laser excitation and fluorescence detection detailed in FIGS. 2-4.

The arrangement of the scanned slides in a ring on the turntable provides an additional benefit of convenience to use not just one fluorescence collection system 92 with a single excitation laser as depicted in FIG. 7, but, rather as best shown in FIG. 8, at least two fluorescence collection systems 92, 96 accessing the slides 10 on the spinning turntable 80 from different sides of the same turntable 80. Each of the systems 92, 96 may be equipped with a different wavelength laser for more reliable detection and location of the rarely occurring cells on the microscope slides.

Figure 9:
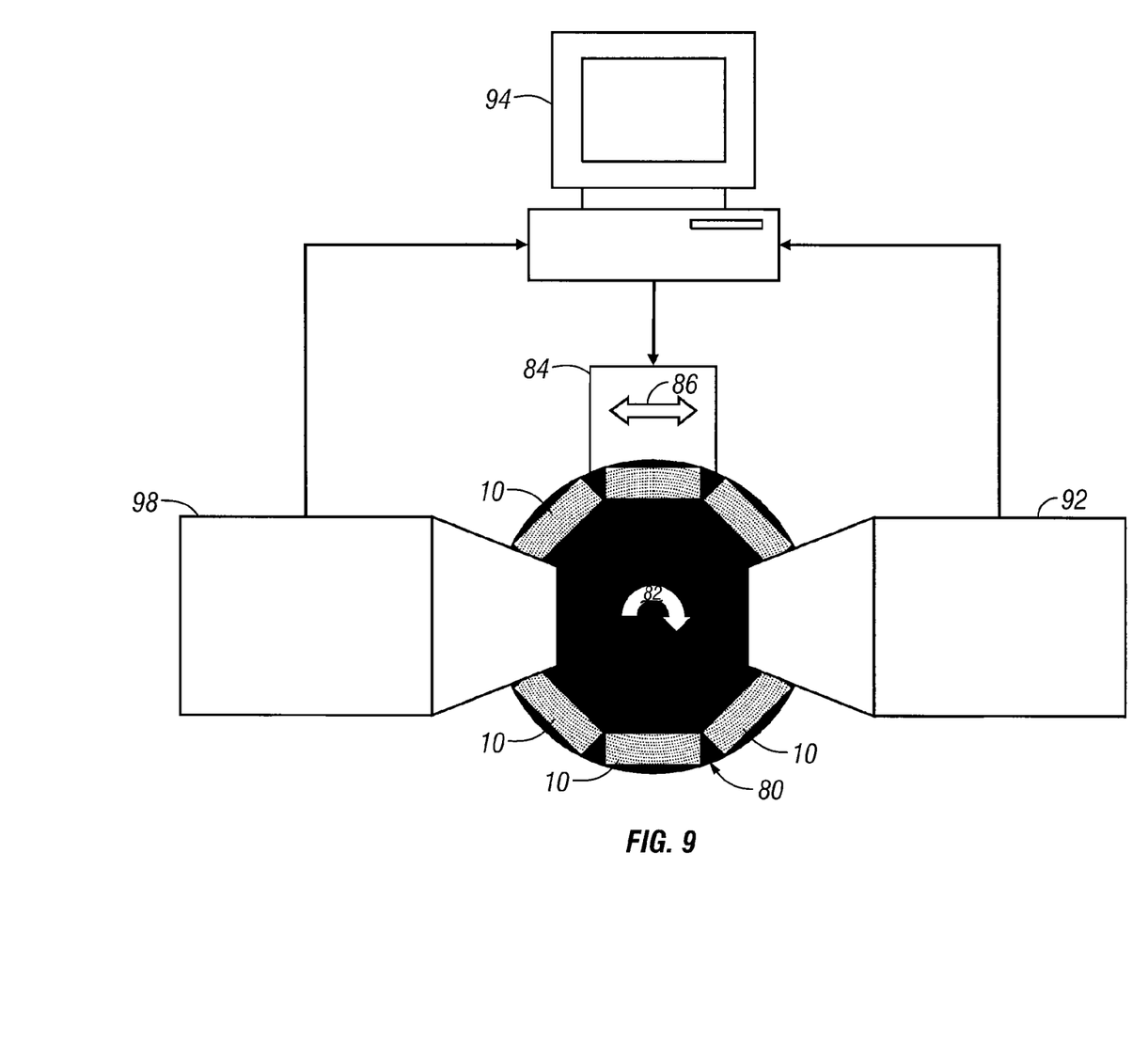
FIG. 9 is a diagram of a computer-controlled system for detection of rare cells deposited on microscope slides placed on the spinning and linearly translated turntable with laser excitation and fluorescence detection detailed in FIGS. 2-4 and an automated digital epi-fluorescence microscope.

Another benefit of the ring arrangement of the multiple slides on a spinning turntable is in the opportunity to present pre-scanned slides to the automated digital epi-fluorescence microscope for further detailed analysis immediately after the prescanning by the laser excitation and fluorescence detection part of the system. As shown in FIG. 9, the automated digital epi-fluorescence microscope 98 can access the slide 10 still mounted on the turntable 80 from the diametrically opposite side. As a result, the slides 10 can be further inspected by the automated digital epi-fluorescence microscope 98 part of the system immediately after the pre-scanning step and without the need to transfer them from the turntable to a microscope stage. The automated digital epi-fluorescence microscope 98 should be of an up-right type for the up-right laser excitation and fluorescence detection configuration and of inverted type for the inverted laser excitation and fluorescence detection configuration correspondingly.

Figure 10:
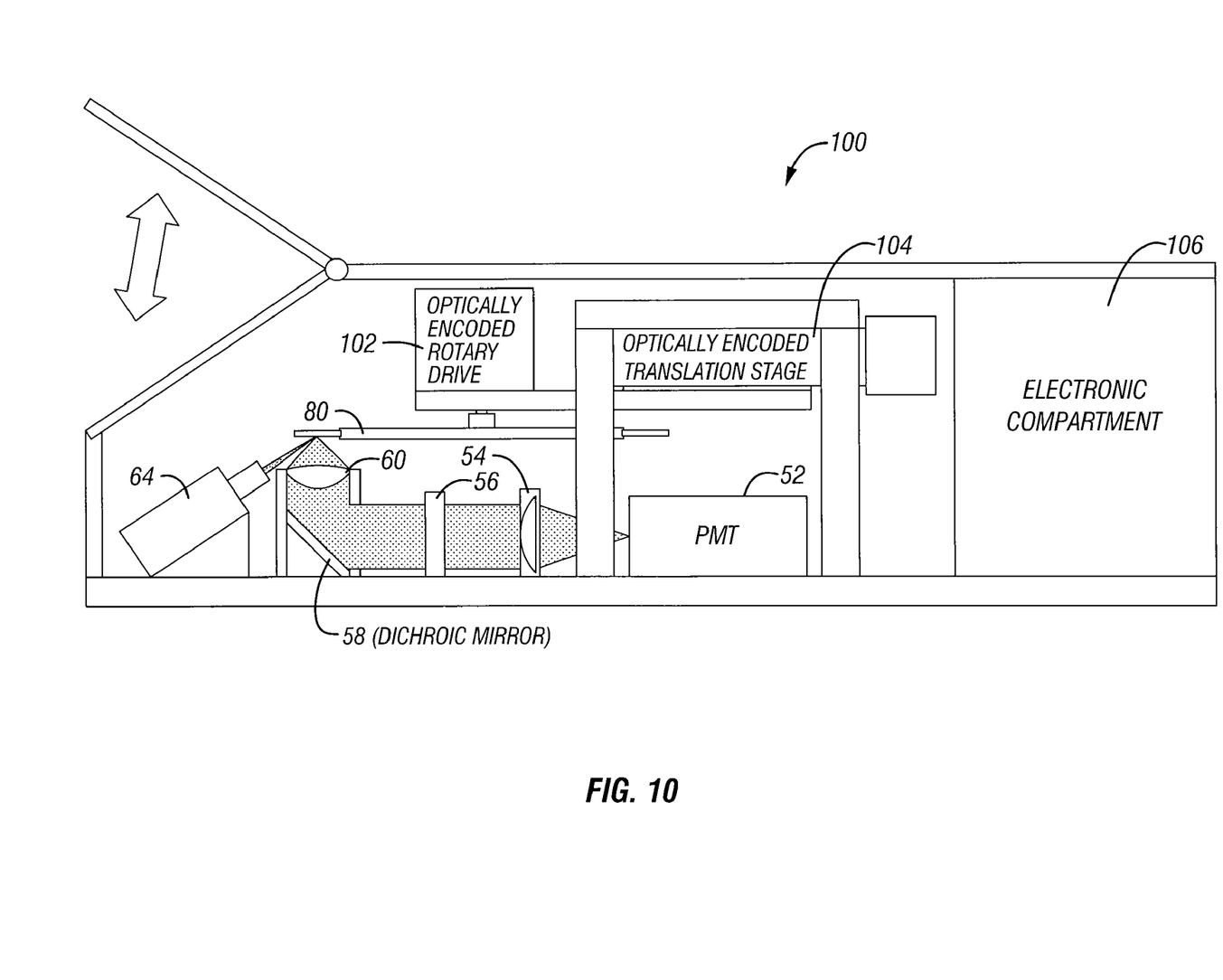
FIG. 10 is a diagram of a computer-controlled system for a beamsplitterless fluorescence excitation and fluorescence collection and detection system with oblique incidence of a laser excitation beam on the surface of the scanned microscope slide with a spinning and linearly translated turntable according to an aspect of the present invention.

FIG. 10 illustrates an embodiment of a computer-controlled system 100 for a beamsplitterless fluorescence excitation and fluorescence collection system with a spinning and linearly translating turntable 80. An optically encoded rotary drive 102 and an optically encoded translation stage 104 are controlled to provide for precise control of the turntable 80. There is an electronics compartment 106 shown for housing electronics. The optical system shown is similar to that of FIG. 4.

Thus, methods, apparatuses, and systems for high throughput detection of rarely occurring events in biological samples have been disclosed. It should be appreciated that the present invention contemplates numerous variations, options, and alternatives and is not to be limited to the specific details of the exemplary embodiments described herein.

What is claimed is:

1. A method of detection of a rarely occurring event within one or more biological samples comprising:
   a. processing each biological sample to provide a gellable liquid solution comprising concentrated biological sample and a flourochrome designed to associate with a rarely occurring event within the concentrated biological sample;
   b. depositing the solution in a layer on a surface of a slide;
   c. scanning the solution on the slide with energy adapted to cause fluorescence of the flourochrome to detect potential instances of the rarely occurring event within the concentrated biological sample in the solution.

2. The method of claim 1 further comprising analyzing the potential instances of the rarely occurring event to filter out potential instances of the rarely occurring event from not actual instances of the rarely occurring event.

3. The method of claim 1 further comprising maintaining location information for potential instances of rarely occurring events.

4. The method of claim 1 wherein the biological sample comprises cells.

5. The method of claim 4 wherein the rarely occurring event is a subset of the cells.

6. The method of claim 5 wherein the subset of the cells comprises cells associated with a disease.

7. The method of claim 1 wherein the gellable liquid solution comprises a polymerizable gel or hydrogel.

8. The method of claim 1 wherein the flourochrome comprises a fluorochrome antibody directed again surface markers specific for the rarely occurring event.

9. The method of claim 8 wherein the flourochrome antibody comprises a fluorescent immunocytochemical stain.

10. The method of claim 1 wherein the step of depositing comprises automated depositing with a robotic liquid handling system.

11. The method of claim 1 wherein the slide is a slide with a raised border to contain the solution.

12. The method of claim 1 further comprising one or more additional layers of solution placed over the layer of solution in the slide to increase the amount of biological sample on the slide.

13. The method of claim 1 wherein the concentration of biological sample is not greater than on the order of one-half the density limit of the slide surface and the biological sample comprises on the order of 75% of utilized surface area of the slide surface.

14. The method of claim 1 wherein the scanning comprises scanning the excitation energy in a beam across the slide.

15. The method of claim 14 further comprising translating the slide relative to the beam.

16. The method of claim 15 wherein the translating comprises one or more of linear translating and rotational translating.

17. The method of claim 14 wherein the beam is focused into an elliptical spot.

18. The method of claim 17 wherein the beam is a laser beam.

19. The method of claim 14 wherein the beam is reflected by a dichroic mirror to the solution on the slide.

20. The method of claim 14 wherein the beam directly intersects the solution on the slide at an oblique angle of incidence.

21. The method of claim 1 further comprising a plurality of slides each with either a solution comprising the biological sample or a solution comprising a different biological sample.

22. The method of claim 21 wherein the plurality of slides are positioned at spaced apart positions on a turntable that rotates relative to the excitation energy.

23. The method of claim 22 wherein the turntable further linearly translates relative to the excitation energy.

24. The method of claim 23 further comprising the excitation energy scans over a distance.

25. A method for detection of a rarely occurring event within one or more biological samples comprising:
  a. processing each biological sample to provide a concentrated sample;
  b. depositing a concentrated sample in a gellable liquid solution on each of a plurality of slides;
  c. mounting the plurality of slides on a rotatable turntable in precisely identified locations;
  d. prescanning the plurality of slides using laser fluorescence excitation and collection to determine potential instances of the rarely occurring event within the concentrated sample;
  e. analyzing the potential instances of the rarely occurring event to filter out potential instances of the rarely occurring event from not actual instances of the rarely occurring event;
  f. maintaining location information for remaining potential instances of the rarely occurring event;
  g. using the location identification information to locate the potential instances of the rarely occurring event for additional analysis; and
  h. providing the additional analysis to detect instances of the rarely occurring event from the remaining potential instances.

26. The method of claim 25 wherein the rotatable turntable is rotating during the prescanning.

27. The method of claim 26 wherein the rotatable turntable is configured to rotate while linearly translating to thereby provide for a spiral path of travel of the scan relative to the slides.

28. The method of claim 25 further comprising the step of allowing the gellable liquid solution to gel after depositing the concentrated sample in a gellable liquid solution on the plurality of slides.

29. The method of claim 25 wherein each of the plurality of slides comprises a bordered area for containing the gellable liquid solution.

30. The method of claim 25 wherein the sample comprises cells.

31. The method of claim 30 wherein the rarely occurring event is associated with a disease.

32. The method of claim 31 wherein the rarely occurring event associated with a disease comprises diseased cells.

33. The method of claim 25 wherein the step of providing the additional analysis is performed using an automated digital epi-fluorescence microscope.

34. The method of claim 25 wherein the step of depositing the concentrated sample in a gellable liquid solution on a slide comprises depositing a plurality of layers of the concentrated sample on the slide.

35. A method for detection of a rarely occurring event within a biological sample comprising:
  providing a system comprising an automated cell dispensing tool for dispensing cells from the biological sample on microscope slides,
  a computer-controlled system for detection of rarely occurring cells on microscope slides using laser excited fluorescence collection; and
  processing each biological sample to provide a gellable liquid solution comprising concentrated biological sample and a flourochrome designed to associate with a rarely occurring event within the concentrated biological sample;
  depositing the solution in a layer on a surface of a slide using the automated cell dispensing tool;
  using the computer-controlled system for scanning the solution on the slide with energy adapted to cause fluorescence of the flourochrome to detect potential instances of the rarely occurring event within the concentrated biological sample in the solution.

* * * * *